United States Patent
Lee et al.

(10) Patent No.: US 6,348,611 B1
(45) Date of Patent: Feb. 19, 2002

(54) PROCESS FOR CARBONYLATION OF EPOXIDE DERIVATIVES

(75) Inventors: Byeong-No Lee, Seoul; Duck-Joo Yang; Young-Hun Byun, both of Taejeon, all of (KR)

(73) Assignee: Samsung Electronic Co., Ktd. (KR)

( * ) Notice: Subject to any disclaimer, the term of this patent is extended or adjusted under 35 U.S.C. 154(b) by 0 days.

(21) Appl. No.: 09/387,713

(22) Filed: Aug. 25, 1999

(30) Foreign Application Priority Data

Mar. 9, 1999 (KR) ............................................. 99-7676

(51) Int. Cl.$^7$ ............................. C07F 17/02; C07F 9/28; B01J 31/00
(52) U.S. Cl. ............................... 556/21; 556/1; 556/28; 556/136; 556/137; 548/402; 546/2; 544/225; 502/152; 502/155; 502/166
(58) Field of Search ................................ 556/21, 28, 1, 556/136, 137; 502/155, 152, 166; 546/2; 548/402; 544/225

(56) References Cited

U.S. PATENT DOCUMENTS

| 4,973,741 A | 11/1990 | Beavers ...................... 560/179 |
| 5,135,901 A | 8/1992 | Beavers ...................... 502/161 |
| 5,310,948 A | 5/1994 | Drent et al. ................. 549/328 |
| 5,359,081 A | 10/1994 | Drent et al. ................. 549/328 |
| 5,723,389 A | 3/1998 | Slaugh et al. ............... 468/862 |
| 5,731,478 A | 3/1998 | Slaugh et al. ............... 568/862 |
| 5,770,776 A | 6/1998 | Powell et al. ............... 568/862 |

OTHER PUBLICATIONS

King et al., Inorganic Chemistry, vol. 8, No. 5, pp. 1042–1048, May 1969.*

R. Bruce King, Organometallic Synthesis, vol. 1, Transition Metal Compounds, Academic Press, New York, 1965.*

Heck, R., "The Reaction of Epoxides with Cobalt Hydrocarbonyl and Cobalt Tetracarbonyl Anion", *J. Am. Chem. Soc.*, 1963, 85, 1460–1463.

Dalcanale, et al., "A New Synthesis of 2-(6-Methoxycarbonylhexyl)-cyclopent-2-en-1-one", *Synthesis*, 1986, 492–493.

Eisenmann, et al., "Preparation of Methyl β-Hydroxybutyrate from Propylene Oxide, Carbon Monoxide, Methanol, and Dicobalt Octacarbonyl", *J. Org. Chem.*, 1961, 26, 2102–2105.

* cited by examiner

*Primary Examiner*—Porfirio Nazario-Gonzalez
(74) *Attorney, Agent, or Firm*—Woodcock Washburn LLP

(57) ABSTRACT

The present invention relates to a process for carbonylation of epoxide derivatives, in which the reactivity, selectivity and the yield are superior. More specifically, the present invention relates to a process for hydroformylation of an epoxide derivative in which there is utilized a transition metal catalyst having a cyclopentadienyl radical, thereby improving the reactivity and selectivity. Further, the present invention relates to a process for hydroesterification of an epoxide derivative, in which a proper catalyst is selected, and the reaction temperature and pressure are adjusted within proper ranges under the presence of a cobalt catalyst, thereby improving the product selectivity and the yield.

3 Claims, No Drawings

PROCESS FOR CARBONYLATION OF EPOXIDE DERIVATIVES

FIELD OF THE INVENTION

The present invention relates to a process for carbonylation of epoxide derivatives, in which the reactivity, selectivity and the yield are superior. More specifically, the present invention relates to a process for hydroformylation of an epoxide derivative in which there is utilized a transition metal catalyst having a cyclopentadienyl radical, thereby improving the reactivity and selectivity. Further, the present invention relates to a process for hydroesterification of an epoxide derivative, in which a proper catalyst is selected, and the reaction temperature and pressure are adjusted within proper ranges in the presence of a cobalt catalyst, thereby improving the product selectivity and the yield.

BACKGROUND OF THE INVENTION

The epoxide derivatives can be easily converted into difunctional compounds through a carbonylation reaction. These difunctional compounds are used as an intermediate of useful organic compounds. Among them, the typical compounds are the 3-hydroxyaldehyde derivatives and the 3-hydroxyester derivatives, the former being synthesized by a hydroformylation of epoxide derivatives, and the latter being synthesized by a hydroesterification of an epoxide derivative. In the 3-hydroxyaldehyde derivatives which are synthesized by the hydroformylation, aldehyde group is converted into an alcohol radical through a hydrogenation, thereby obtaining alkanediol. Among the alkanediol derivatives, 1,3-propanediol is known to be an intermediate for synthesizing the polyester which is used for making fibers and films. Further, it is also used as an intermediate for coating materials and for organic synthesis. Meanwhile the 3-hydroxyester derivatives which are obtained by the hydroesterification of the epoxide derivatives have two active radicals, respectively. Therefore, they are known to be useful as solvents, resins and coating materials. Further, they can be converted into other compounds, so that they can be used in the medical field. Further, they are also used as an intermediate for synthesizing the alkanediols. In a known process for synthesizing the 3-hydroxyaldehyde showing a high selectivity under a low temperature and a low pressure, there are used a cobalt catalyst and phosphine oxide ligand as a promoter. However, when phosphine oxide ligand is used as a promoter, the recovery and regeneration of the catalyst become complicated.

U.S. Pat. Nos. 5,770,776, 5,723,389 and 5,731,478 disclose processes in which ethylene oxide is hydroformylated, and a hydrogenation of aldehyde group is adopted. In these processes, a cobalt catalyst is used, and another metal compound or ligand is used as the promoter instead of the phosphine oxide ligand, thereby improving the activity and the selectivity of the cobalt catalyst.

U.S. Pat. Nos. 5,135,901 and 4,973,741 disclose another process for obtaining the 3-hydroxyester derivative from the epoxide derivatives. In this process, there is synthesized methyl 3-hydroxypropionate from ethylene oxide by using rhodium and ruthenium as catalysts in the presence of carbon monoxide and alcohol. However, in this process, in spite of the use of expensive catalysts, the yield of the 3-hydroxypropionate is as low as 60%, and by-products are produced in considerable amounts. Further, there is another known process for obtaining a 3-hydroxyester by hydroesterification of the epoxide. In this process also, the yield is as low as 40–60%. [(1) Dalcanali, E.; Foa, M. Synthesis 1986, 492. (2) Heck, R. F., J. Am. Chem. Soc., 1963, 85, 1460. (3) Eismann, J. L.; Yamartino, R. L.; Howard, Jr. J. F., J. Org. Chem. 1961, 2102.]. The reason why the yield is so low is that the isomerization reaction of the starting material readily occurs.

Meanwhile, U.S. Pat. Nos. 5,310,948 and 5,359,081 relate to a carbonylation of the epoxide, in which the epoxide and carbon monoxide are reacted in the presence of cobalt and pyridine derivatives. The final product is mainly -lactone, and the by-product is the 3-hydroxyester.

As described above, there has not yet been found an effective process for synthesizing the 3-hydroxyester derivative, in which economy is ensured.

Therefore, the present inventors have conducted studies on the carbonylation of epoxides for obtaining an intermediate which is useful for synthesizing an organic compound and alkanediol. For this purpose, a transition metal compound in which a cyclopentadiene radical had been coupled to a 9th group transition metal was made to react with a compound having one or more active radicals. The compound thus obtained was used as a catalyst in the presence of a cobalt compound to obtain 3-hydroxyaldehyde derivatives with a high reactivity and selectivity, thereby establishing a process for hydroformylation. Further, an epoxide derivative was made to react with carbon monoxide and alcohol in the presence of a proper solvent and a cobalt catalyst, and the reaction temperature and pressure were adjusted to proper levels to obtain a 3-hydroxyester derivative with a high yield, thereby establishing a process for hydroesterification.

SUMMARY OF THE INVENTION

It is an object of the present invention to provide transition metal catalysts which show superior reactivity and selectivity in the hydroformylation of epoxide derivatives.

It is another object of the present invention to provide transition metal catalysts which show superior recovery and regeneration characteristics in the hydroformylation of epoxide derivatives.

It is still another object of the present invention to provide a process for hydroformylation of epoxide derivatives, in which a cobalt compound and a transition metal compound with superior reactivity and selectivity are used, thereby synthesizing a 3-hydroxyaldehyde derivative with high selectivity and yield.

It is still another object of the present invention to provide a process for hydroesterification of epoxide derivatives, in which a proper solvent and a cobalt catalyst are used, and the reaction temperature and pressure are adjusted to proper ranges, thereby synthesizing 3-hydroxyester derivatives with a high yield.

In the present invention, there is provided a process for carbonylation of epoxide derivatives for synthesizing 3-hydroxyaldehyde derivatives and 3-hydroxyester derivative which are the useful intermediates are used for synthesizing organic compounds and alkanediols.

In achieving the above objects, the present invention is characterized as follows. That is, the 3-hydroxyaldehyde derivatives are synthesized by a hydroformylation of epoxide derivatives. The hydroformylation reactions are carried out in the following manner. A cobalt compound and a transition metal compound having a cyclopentadienyl radical (which is separately synthesized) are dissolved in a non-aqueous solvent. Then, an epoxide derivative is added, then carbon monoxide and hydrogen (CO/H$_2$) are introduced into the reactor, and then, the reactor is put into an oil bath which is maintained at a desired temperature. Alternatively, a transition metal compound having the above mentioned cyclopentadienyl radical is synthesized in a non-aqueous solvent, and then, the hydroformylation process is carried out without any separating step.

DETAILED DESCRIPTION OF THE PREFERRED EMBODIMENT

The mole ratios of the cobalt compound to the transition metal having the cyclopentadienyl radical are preferably 1000:1~1:5, and more preferably 100:1~1:2. The mole ratio of CO/H$_2$ which are supplied for the hydroformylation is preferably 3/1~1/10, and more preferably 2/1~1/5. The total pressure is preferably 100~3000 psi, and more preferably 500~2000 psi. The temperature is raised from the normal temperature to 30 degrees C.~120 degrees C., and more preferably to 60~100 degrees C. in proceeding the hydroformylation.

Now the catalyst, the solvent and the epoxide derivatives which are used in the hydroformylation of the present invention will be described in detail.

The transition metal catalysts which are used in the hydroformylation are transition metal compounds which are prepared by bonding the 9th group transition metal to the cyclopentadienyl radical. Or it is one of those compounds which are synthesized by reacting the above mentioned transition metal compound with a compound having one or more active radicals. The transition metal compounds may be bonded with ligands other than the cyclopentadienyl radical, and this is expressed by at least one of the following formulas:

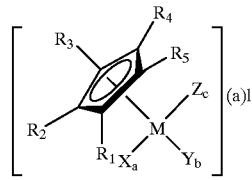

(A-1)

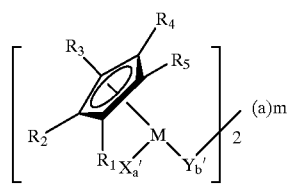

(A-2)

The compounds belonging to (A-1) are neutral or cationic, M represents the 9th group transition metals such as cobalt, rhodium, and iridium, and the oxidation state of the metal is 1 or 3;

(a) is: a 1-valence anion of BF$_4$—, PF$_6$—, ClO$_4$—, SO$_3$CF$_3$— or BR'$_4$— (R' representing: hydrogen; or an alkyl radical of saturated or unsaturated aliphatic chain type or ring type hydrocarbons or aromatic hydrocarbons having C$_1$~C$_{10}$); a halogen atom of F, Cl, Br or I; or a 2-valence anion of CO$_3^{2-}$ or SO$_4^{2-}$;

l is an integer of 0–2 in case where (a) is a 1-valence anion or a halogen atom, and is 0–1 in case where (a) is a 2-valence anion;

R$_1$~R$_5$ are hydrogen; saturated or unsaturated aliphatic or aromatic hydrocarbons of C$_1$~C$_{20}$, or saturated or unsaturated aliphatic or aromatic hydrocarbons having nitrile radicals at the end or at the middle, or having amine radicals at the end or at the middle; or a halogen atom of F, Cl, Br or I;

a, b and c in X$_a$, Y$_b$ and Z$_c$ are integers of 0~3, with a+b+c=3;

X$_a$, Y$_b$ and Z$_c$, respectively, are carbon monoxide; a halogen atom of F, Cl, Br or I; hydroxy radical; aliphatic or aromatic hydrocarbon having no branch at C$_1$~C$_{10}$; aliphatic or aromatic hydrocarbon having branches at C$_1$~C$_{10}$; hydroxy radical including aliphatic or aromatic hydrocarbons with branches at C$_1$~C$_{10}$; saturated or unsaturated aromatic hydrocarbon of C$_1$~C$_{10}$, or a nitrile including aliphatic hydrocarbons with saturated or unsaturated aliphatic chains; a ketone including aliphatic hydrocarbons or aliphatic chain type or ring type hydrocarbons of C$_1$~C$_{20}$; ether including aliphatic hydrocarbons or aliphatic chain type or ring type hydrocarbons of C$_1$~C$_{20}$; an amine expressed by N(R$_6$)(R$_7$)(R$_8$) (here, R$_6$, R$_7$ and R$_8$ respectively representing hydrogen or alkyl radicals including carbon chains of saturated or unsaturated aliphatic hydrocarbons or aliphatic chain type or ring type hydrocarbons of C$_1$~C$_{20}$); pyrrole, pyrazine, pyrazole, imidazole, pyrimidine, piperidine, pyridine or their derivatives, all of them having C$_3$~C$_{30}$; or compounds expressed by the following formulas, or their mixtures:

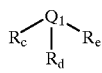

(I)

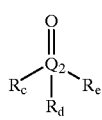

(II)

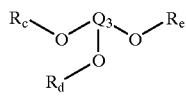

(III)

wherein, Q$_1$ represents N, P, As or Sb;

Q$_2$ and Q$_3$ are P, As or Sb;

Rc, Rd and Re are hydrogen or alkyl radicals including saturated or unsaturated aliphatic or aromatic chain type or ring type hydrocarbons of C$_1$~C$_{20}$, or aromatic hydrocarbons, or preferably hydrogen; aliphatic hydrocarbons (cyclohexyl or carbon chains of C$_1$~C$_5$); phenyl or benzyl; compounds including at least one or more of nitrile radicals, amine radicals of R$_f$R$_g$N—, aldehyde radicals or ketone radicals in the aliphatic hydrocarbon or in phenyl or in benzyl (R$_f$ and R$_g$ represent hydrogen; or alkyl radicals including saturated or unsaturated aliphatic or aromatic chain type or ring type hydrocarbons of C$_1$~C$_{20}$, or aliphatic hydrocarbons, or preferably carbon chains of C$_1$~C$_{10}$ having no branches, carbon chains having branches, ring type compounds, or aliphatic hydrocarbons; f and g being integers of 0~2, with f+g=2); a halogen atom of F, Cl, Br or I; phosphine radicals, arsine radicals or stibine radicals including saturated or unsaturated aliphatic or aromatic chain type or ring type hydrocarbons or aromatic hydrocarbons of C$_1$~C$_{30}$; and in the Rc, Rd and Re, c, d, and e are integers of 0~3, with c+d+e=3.

In the formula (A-2), M, (a) and $R_1 \sim R_5$ are the same as defined in (A-1);

m is an integer of 0, 2 or 4 in the case where (a) is a 1-valence anion or a halogen atom, or is an integer of 0, 1, or 2 in the case where (a) is a valence-2 anion;

$X_{a'}$ is a halogen atom of F, Cl, Br or I; a hydroxy radical; alkoxy including saturated or unsaturated aliphatic or aromatic hydrocarbons of $C_1 \sim C_{10}$; a nitrile including saturated or unsaturated aliphatic or aromatic hydrocarbons of $C_1 \sim C_{10}$; or a compound expressed by the above formulas (I), (II) or (III); and $Y_{b'}$ is a carbon monoxide; a halogen atom of F, Cl, Br or I; a hydroxy radical; or an alkoxy radical including saturated or unsaturated aliphatic or aromatic hydrocarbons of $C_1 \sim C_{10}$, such a compound being one furnishing the electrons dually.

The transition metal compounds which are expressed by the formulas (A-1) and (A-2) can be used as a catalyst together with a cobalt compound during the hydroformylation. Or the compounds can be used as a catalyst when a new compound obtained by reacting with a compound having one or more active radicals is hydroformylated together with a cobalt compound. The transition metal compounds of the present invention and the synthesized compounds as described above can be used as a promoter together with the cobalt catalyst to improve the catalyst activity and the selectivity. The above mentioned compounds having one or more active radicals are expressed by the following formulas:

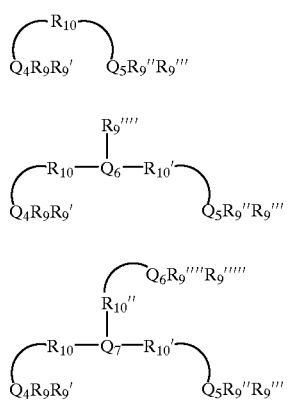

wherein, $Q_4$, $Q_5$, $Q_6$, and $Q_7$ respectively are N, P, As or Sb;

$R_9$, $R_9'$, $R_9''$, $R_9'''$, $R_9''''$ and $R_9'''''$ are hydrogen; aliphatic hydrocarbons, aromatic hydrocarbons, or both of the aliphatic and aromatic hydrocarbons of $C_1 \sim C_{20}$, or preferably hydrogen; aliphatic hydrocarbons ($C_1 \sim C_5$ carbon chains or cyclohexyl); phenyl or benzyl; compounds including at least one or more of nitrile radicals, amine radicals of $R_f R_g N$—, aldehyde radicals or ketone radicals in the aliphatic hydrocarbon or in phenyl or in benzyl ($R_f$ and $R_g$ respectively represent hydrogen; or alkyl radicals including saturated or unsaturated aliphatic or aromatic chain type or ring type hydrocarbons of $C_1 \sim C_{20}$, or aliphatic hydrocarbons, or preferably carbon chains of $C_1 \sim C_{10}$ having no branches, carbon chains having branches, ring type compounds, or aliphatic hydrocarbons; and f and g being integers of 0~2, with f+g=2); a halogen atom of F, Cl, Br or I; phosphine radicals, arsine radicals or stibine radicals including aliphatic or aromatic chain type or ring type hydrocarbons or aromatic hydrocarbons of $C_1 \sim C_{30}$; and $R_{10}$, $R_{10}'$ and $R_{10}''$ are alkyl radicals including carbon chains of saturated or unsaturated aliphatic chain type or ring type hydrocarbons or aromatic hydrocarbons having $C_1 \sim C_{20}$, and preferably carbon chains of $C_1 \sim C_{10}$ having no branches, carbon chains having branches, ring type compounds, or aromatic hydrocarbons.

The transition metal compounds of formulas (A-1) and (A-2) can be reacted with the compounds of the formulas (B-1), (B-2) and (B-3) having one or more active radicals, so that a transition metal catalyst can be obtained as expressed by formulas (C-1), (C-2), (C-3), (C-4) and (C-5) below.

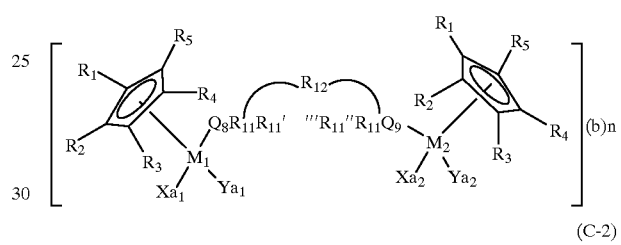

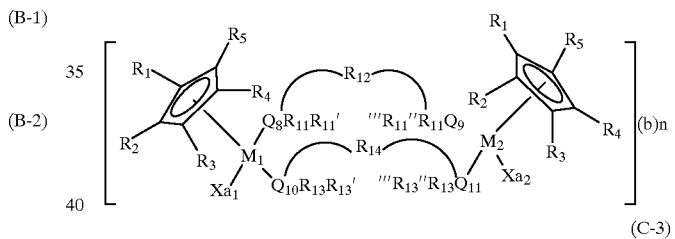

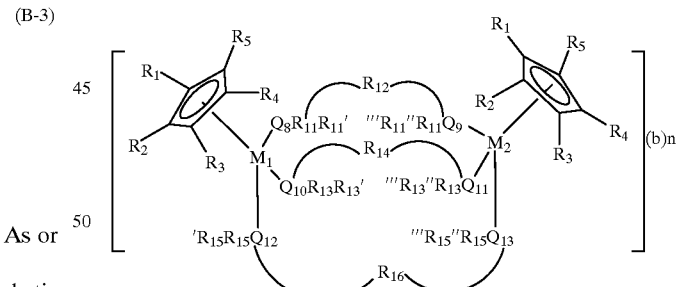

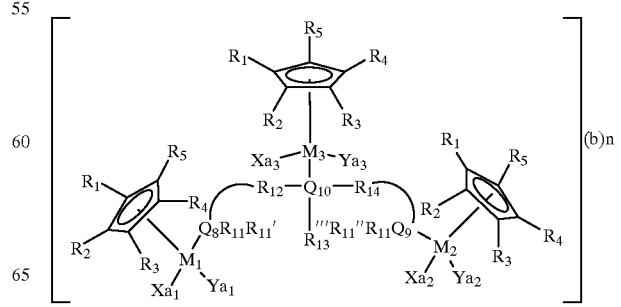

-continued

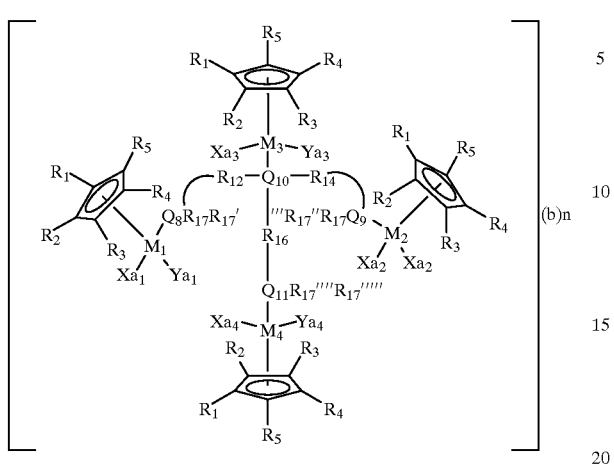

(C-5)

wherein, $M_1$, $M_2$, $M_3$ and $M_4$ are the 9th group transition metals such as cobalt, rhodium or iridium, their valence being 1 or 3;

(b) is 1-valence anions $BF_4-$, $PF_6-$, $ClO_4-$, $SO_3CF_3-$ or $BR'_4$ ($R'$ is hydrogen; or alkyl radical of saturated or unsaturated aliphatic chain or ring type hydrocarbons or aromatic hydrocarbons having $C_1 \sim C_{10}$); a halogen atom of F, Cl, Br or I; or valence-2 anions of $CO_3^{2-}$ or $SO_4^{2-}$;

n is an integer of 0~8 in the case where (b) is 1- valence anion, and an integer of 0~4 in the case where (b) is a 2-valence anion;

$R_1 \sim R_5$ are hydrogen; saturated or unsaturated aliphatic or aromatic hydrocarbons of $C_1 \sim C_{20}$, or saturated or unsaturated aliphatic or aromatic hydrocarbons having nitrile radicals at the end or at the middle, or having amine radicals at the end or at the middle; or a halogen atom of F, Cl, Br or I;

$X_{a1}$, $X_{a2}$, $X_{a3}$, $X_{a4}$, $Y_{a1}$, $Y_{a2}$, $Y_{a3}$, and $Y_a$ respectively are carbon monoxide; halogen atom of F, Cl, Br or I; hydroxy radicals; aliphatic or aromatic hydrocarbons having no branch at $C_1 \sim C_{10}$; aliphatic or aromatic hydrocarbons having branches at $C_1 \sim C_{10}$; alkoxy including aliphatic or aromatic hydrocarbons with branches at $C_1 \sim C_{10}$; nitrile radicals including saturated or unsaturated aliphatic hydrocarbons of $C_1 \sim C_{10}$, or nitrile radicals including aliphatic hydrocarbons with saturated or unsaturated aliphatic chains; ketone including aromatic hydrocarbons or aliphatic chain type or ring type hydrocarbons of $C_1 \sim C_{20}$; ether including aromatic hydrocarbons or aliphatic chain type or ring type hydrocarbons of $C_1 \sim C_{20}$; amine expressed by $N(R_6)(R_7)(R_8)$ (here, $R_6$, $R_7$ and $R_8$ respectively represent hydrogen or alkyl radicals including carbon chains of saturated or unsaturated aromatic hydrocarbons or aliphatic chain type or ring type hydrocarbons of $C_1 \sim C_{20}$); pyrrole, pyrazine, pyrazole, imidazole, pyrimidine, piperidine, pyridine or their derivatives, all of them having $C_3 \sim C_{30}$; or compounds expressed by the formulas (I), (II) or (III), or their mixtures:

$Q_8$, $Q_9$, $Q_{10}$, $Q_{11}$, $Q_{12}$ and $Q_{13}$ respectively are N, P, As or Sb;

$R_{11}$, $R_{11}'$, $R_{11}''$, $R_{11}'''$, $R_{13}$, $R_{13}'$, $R_{13}''$, $R_{13}'''$, $R_{15}$, $R_{15}'$, $R_{15}''$, $R_{15}'''$, $R_{17}$, $R_{17}'$, $R_{17}''$, $R_{17}'''$, $R_{17}''''$ and $R_{17}'''''$ are hydrogen; alkyl radicals including saturated or unsaturated aliphatic or aromatic chain type or ring type hydrocarbons of $C_1 \sim C_{20}$, or aromatic hydrocarbons, or preferably hydrogen; aromatic hydrocarbons (cyclohexyl or carbon chains of $C_1 \sim C_5$); phenyl or benzyl; compounds including at least one or more of nitrile radicals, amine radicals of $R_f R_g N-$, aldehyde radicals or ketone radicals in the aromatic hydrocarbon or in phenyl or in benzyl ($R_f$ and $R_g$ respectively represent hydrogen; or alkyl radicals including saturated or unsaturated aliphatic or aromatic chain type or ring type hydrocarbons of $C_1 \sim C_{20}$, or aromatic hydrocarbons, or preferably carbon chains of $C_1 \sim C_{10}$ having no branches, carbon chains having branches, ring type compounds, or aromatic hydrocarbons; and f and g being integers of 0~2, with f+g=2); compounds including one or more aldehyde radicals or ketone radicals; a halogen atom of F, Cl, Br or I; phosphine radicals, arsine radicals or stibine radicals including saturated or unsaturated aliphatic or aromatic chain type or ring type hydrocarbons or aromatic hydrocarbons of $C_1 \sim C_{30}$; and $R_{12}$, $R_{14}$ and $R_{16}$ are alkyl radicals of saturated or unsaturated aliphatic chain or ring type hydrocarbons or aromatic hydrocarbons having $C_1 \sim C_{20}$, or preferably carbon chains of $C_1 \sim C_{10}$ having no branches, carbon chains having branches, ring type compounds or aromatic hydrocarbons.

The typical example of the cobalt compound which is used together with the transition metal catalyst having a cyclopentadienyl radical is $Co_2(CO)_8$. This transition metal catalyst is used dissolved in an etherial non-aqueous solvent at a certain mole ratio relative to a cobalt compound as shown below:

(D)

wherein, $R_{18}$ and $R_{19}$ respectively are aliphatic hydrocarbons of $C_1 \sim C_{20}$ having no branches, aliphatic hydrocarbons having branches, aromatic hydrocarbons, or hydrocarbons including both of the aliphatic and aromatic hydrocarbons.

Preferably the solvent is methyl-t-butyl ether (MTBE), and it is desirable to use it after saturating it with water.

The epoxide derivatives which are used in the present invention are expressed by the following formula (E):

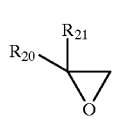

(E)

wherein, $R_{20}$ and $R_{21}$ are hydrogen; aliphatic hydrocarbons of $C_1 \sim C_{20}$ having no branches; aliphatic hydrocarbons having branches; saturated ring type hydrocarbons; chain type hydrocarbons having a ring; aliphatic hydrocarbons having aromatic rings; hydrocarbons of one or more carbons with the hydrogen substituted by F or Cl; hydrocarbons with no substituted radicals; or aromatic hydrocarbons with the hydrogen of aromatic ring substituted by F, Cl, amine radical, nitrile radical, or alkoxy radical.

The desirable examples of the epoxide derivatives include aromatic compounds and compounds having aromatic rings such as ethylene oxide, propylene oxide, 1-butane oxide, 1-pentane oxide, 1-heptane oxide, 1-octane oxide, 1-nonane oxide, 1-decane oxide, 2-methyl-propylene oxide, 2-methyl- 1-butane oxide, 2-methyl-1-octane oxide, 2-methyl-nonane oxide, 2-methyl-1-decane oxide, 2-methyl-1-butane oxide, 2-methyl-1-pentane oxide, 2-methyl-1-hexane oxide, 2-ethyl-1-heptane oxide, 2-ethyl-1-octane oxide, 2-ethyl-1-nonane oxide, 2-ethyl-1-decane oxide, a compound with one of its hydrogen substituted by carbons of $C_1 \sim C_5$, aryl-benzene oxide, 2-methyl-aryl-benzene oxide, and styrene oxide.

The epoxide derivatives which are expressed by the formula (E) are hydroformylated to form a 3-hydroxyaldehyde derivative which is a kind of carbonyl compound. The 3-hydroxyaldehyde derivatives can be expressed by a formula (F) as shown below:

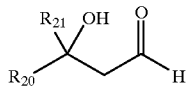

(F)

wherein, $R_{20}$ and $R_{21}$ are the same as those of formula (E).

In the reaction mixture of the hydroformylation of the present invention, besides the carbonyl compound (F), there is formed a small amount of alkanediol in which hydrogenation has occurred to the carbonyl radical. Further, there are produced small amounts of acetic aldehyde, acetone, and methyl-ethyl-ketone through the isomerization reaction of the epoxide, in accordance with the kinds of the epoxide.

The 3-hydroxyester derivatives, which can be used as the precursor of the alkanediol like the 3-hydroxyaldehyde derivatives, are synthesized through the hydroesterification of the epoxide derivatives. The hydroesterification is proceeded in such a manner that the epoxide derivatives are reacted with carbon monoxide and alcohol in the presence of a proper solvent. Under these conditions, the reaction temperature is preferably 30~130 degrees C., and more preferably 40~110 degrees C. During the reaction, the CO pressure is preferably 100~3000 psi, and more preferably 200~1500 psi.

The above epoxide derivatives are the same as those of the compound (E) which is used in the hydroformylation reaction.

The alcohol is expressed by R"OH. Here, R" is a saturated or unsaturated linear hydrocarbon of $C_1 \sim C_{20}$, a hydrocarbon having branches, a ring type hydrocarbon, an aromatic hydrocarbon, or a linear hydrocarbon including an aliphatic, or preferably methyl, ethyl, isopropyl, cyclohexyl, phenyl or benzyl.

The typical example of the cobalt catalyst is $Co_2(CO)_8$, and a promoter may be used in order to enhance the reaction. Under this condition, the concentration of the formed product is adjusted to 1~50 wt % of the total solution, and preferably to 5~40 wt %.

The solvent may be an etherial compound expressed by any one of the following formulas (G-1), (G-2) and (G-3), or may be a compound expressed by the following formula (G-4). Or R"OH which is reactable with the epoxide derivative, may be directly used as a solvent.

$R_{22}$—O—$R_{23}$ (G-1)

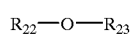

(G-2)

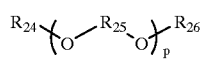

(G-3)

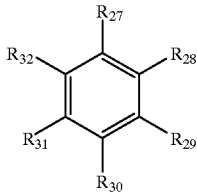

(G-4)

In the formulas (G-1), (G-2), (G-3) and (G-4), $R_{22}$, $R_{23}$, $R_{24}$, $R_{25}$, and $R_{26}$ are saturated aliphatic hydrocarbons of $C_1 \sim C_{10}$ having no branches; aliphatic hydrocarbons having branches; saturated ring type hydrocarbons; chain type hydrocarbons having rings; or aliphatic hydrocarbons having aromatic rings;

$R_{27}$, $R_{28}$, $R_{29}$, $R_{30}$, $R_{31}$ and $R_{32}$ are hydrogen; saturated hydrocarbons of $C_1 \sim C_4$ having branches or no branches; F or Cl; alkoxy radical having $C_1 \sim C_3$; and p is an integer of 1~10, and q is an integer of 2~5.

In the case where a solvent of one of the formulas (G-1) to (G-4) is used, first a 3-hydroxyester derivative is synthesized, and this product is separated by using water. In the case where the solvent is an alcohol, particularly in the case where the solvent is methyl, ethyl, or isopropyl alcohol, the product is separated by evaporation of the solvent. If the solvent is an alcohol having more than four carbon atoms, the separation is carried out using water.

The 3-hydroxyesters which are obtained through the hydroesterification of the epoxide derivatives, according to the present invention is expressed by the following formula (H-1) or (H-2):

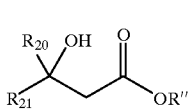

(H-1)

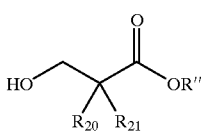

(H-2)

wherein, $R_{20}$, $R_{21}$ and R" are as described above.

During the hydroesterification of the present invention, besides the carbonyl compound [(H-1) or (H-2)], there are formed isomers and auxiliary products depending on the kinds of the epoxide derivatives.

The present invention will be more thoroughly understood by the below described actual examples. These examples are not intended to limit the scope of the present invention, but are just for specifically presenting the present invention to help understanding the present invention.

EXAMPLE 1~13

Synthesis of Iridium Metal Catalysts 1~13
* All the rhodium analogues were prepared in the same manner as described below.

EXAMPLE 1

Synthesis of Catalyst 1
(IrCp*Cl$_2$PPh$_2$CH$_2$CH$_2$CH$_2$CH$_2$PPh$_2$IrCp*Cl$_2$)

A [IrCp*Cl$_2$] compound in an amount of 0.5 g (0.628 mmol) (Cp*=pentamethyl cyclopentadienyl) and a solvent (methylene chloride) in an amount of 50 mL were put into a 100-mL one-sphere flask having an arm and a condenser, so that the compound was dissolved in the solvent. Then 0.27 g (0.63 mmol) of PPh$_2$CH$_2$CH$_2$CH$_2$CH$_2$PPh$_2$ was added to it, then the temperature was raised, then a reflux was carried out for 3~5 hours, and then the volume of the solvent was reduced to 10 mL under a vacuum. Then the orange-colored precipitate was separated by adding 20 mL of diethylether. The yield of the final product was 95~98%.

EXAMPLE 2

Synthesis of Catalyst 2
(IrCp*Cl$_2$PPh$_2$CH$_2$CH$_2$CH$_2$PPh$_2$IrCp*Cl$_2$)

A [IrCp*Cl$_2$]$_2$ compound in an amount of 0.5 g (0.628 mmol) (Cp*=pentamethyl cyclopentadienyl) and a solvent (methylene chloride) in an amount of 50 mL were put into a 100-mL one-sphere flask having an arm and a condenser, so that the compound was dissolved in the solvent. Then 0.260 g (0.628 mmol) of PPh$_2$CH$_2$CH$_2$CH$_2$PPh$_2$ was added to it, then the temperature was raised, then a reflux was carried out for 3~5 hours, and then the volume of the solvent was reduced to 10 mL under a vacuum. Then the orange-colored precipitate was separated by adding 20 mL of diethylether. The yield of the final product was 95~96%.

EXAMPLE 3

Synthesis of Catalyst 3
(IrCp*Cl$_2$PPh$_2$CH$_2$CH$_2$PPh$_2$IrCp*Cl$_2$)

A [IrCp*Cl$_2$]$_2$ compound in an amount of 0.5 g (0.628 mmol) (Cp*=pentamethyl cyclopentadienyl) and a solvent (methylene chloride) in an amount of 50 mL were put into a 100-mL one-sphere flask having an arm and a condenser, so that the compound was dissolved in the solvent. Then 0.25 g (0.628 mmol) of PPh$_2$CH$_2$CH$_2$PPh$_2$ was added to it, then the temperature was raised, then a reflux was carried out for 3–5 hours, and then the volume of the solvent was reduced to 10 mL under a vacuum. Then the orange-colored precipitate was separated by adding 20 mL of diethylether. The yield of the final product was 96~98%.

EXAMPLE 4

Synthesis of Catalyst 4
(IrCp*Cl$_2$PPh$_2$CH$_2$PPh$_2$IrCp*Cl$_2$)

A [IrCp*Cl$_2$]$_2$ compound in an amount of 0.5 g (0.628 mmol) (Cp*=pentamethyl cyclopentadienyl) and a solvent (methylene chloride) in an amount of 50 mL were put into a 100-mL one-sphere flask having an arm and a condenser, so that the compound was dissolved in the solvent. Then 0.241 g (0.628 mmol) of PPh$_2$CH$_2$PPh$_2$ was added to it, then the temperature was raised, then a reflux was carried out for 3~5 hours, and then the volume of the solvent was reduced to 10 mL under a vacuum. Then the orange-colored precipitate was separated by adding 20 mL of diethylether. The yield of the final product was 96~97%.

EXAMPLE 5

Synthesis of Catalyst 5
(IrCp*Cl$_2$PCy$_2$CH$_2$CH$_2$PCy$_2$IrCp*Cl$_2$)

A [IrCp*Cl$_2$]$_2$ compound in an amount of 0.5 g (0.628 mmol) (Cp*=pentamethyl cyclopentadienyl) and a solvent (methylene chloride) in an amount of 50 mL were put into a 100-mL one-sphere flask having an arm and a condenser, so that the compound was dissolved in the solvent. Then 0.265 g (0.628 mmol) of PCy$_2$CH$_2$CH$_2$PCy$_2$ was added to it, then the temperature was raised, then a reflux was carried out for 3~5 hours, and then the volume of the solvent was reduced to 10 mL under a vacuum. Then the orange-colored precipitate was separated by adding 20 mL of diethylether. The yield of the final product was 95~97%.

EXAMPLE 6

Synthesis of Catalyst 6 (IrCp*Cl$_2$(pyridine))

A [IrCp*Cl$_2$]$_2$ compound in an amount of 0.5 g (0.628 mmol) (Cp*=pentamethyl cyclopentadienyl) and a solvent (methylene chloride) in an amount of 50 mL were put into a 100-mL one-sphere flask having an arm, so that the compound was dissolved in the solvent. Then 0.1 g (1.3 mmol) of pyridine was added to it, then an agitation was carried out for 3~5 hours, and then the volume of the solvent was reduced to 10 mL under a vacuum. Then the yellow precipitate was separated by adding 20 mL of diethylether. The yield of the final product was 93~95%.

EXAMPLE 7

Synthesis of Catalyst 7 (IrCp*Cl$_2$P(CH$_2$CH$_2$CN)$_3$)

A [IrCp*Cl$_2$]$_2$ compound in an amount of 0.5 g (0.628 mmol) (Cp*=pentamethyl cyclopentadienyl) and a solvent (methylene chloride) in an amount of 50 mL were put into a 100-mL one-sphere flask having an arm, so that the compound was dissolved in the solvent. Then 0.263 g (1.3 mmol) of P(CH$_2$CH$_2$CN)$_3$ was added to it, then an agitation was carried out for 1~2 hours, and then the volume of the solvent was reduced to 10 mL under a vacuum. Then the orange-colored precipitate was separated by adding 20 mL of diethylether. The yield of the final product was 94~96%.

EXAMPLE 8

Synthesis of Catalyst 8 (IrCp*Cl$_2$PPh$_3$)

A [IrCp*Cl$_2$]$_2$ compound in an amount of 0.5 g (0.628 mmol) (Cp*=pentamethyl cyclopentadienyl) and a solvent (methylene chloride) in an amount of 50 mL were put into a 100-mL one-sphere flask having an arm, so that the compound was dissolved in the solvent. Then 0.341 g (1.3 mmol) of PPh$_3$ was added to it, then an agitation was carried out for 6~7 hours, and then the volume of the solvent was reduced to 10 mL under a vacuum. Then the orange-colored precipitate was separated by adding 20 mL of diethylether. The yield of the final product was 96~98%.

EXAMPLE 9

Synthesis of Catalyst 9 (IrCp*Cl$_2$PCy$_3$)

A [IrCp*Cl$_2$]$_2$ compound in an amount of 0.5 g (0.628 mmol) (Cp*=pentamethyl cyclopentadienyl) and a solvent (methylene chloride) in an amount of 50 mL were put into a 100-mL one-sphere flask having an arm, so that the compound was dissolved in the solvent. Then 0.364 g (1.3 mmol) of PCy$_3$ was added to it, then an agitation was carried out for 2~3 hours, and then the volume of the solvent was reduced to 10 mL under a vacuum. Then the orange-colored precipitate was separated by adding 20 mL of diethylether. The yield of the final product was 95~97%.

EXAMPLE 10

Synthesis of Catalyst 10 (IrCp*Cl$_2$(CO))

A [IrCp*Cl$_2$]$_2$ compound in an amount of 0.5 g (0.628 mmol) (Cp*=pentamethyl cyclopentadienyl) and a solvent (methylene chloride) in an amount of 50 mL were put into a 100-mL one-sphere flask having an arm, so that the compound was dissolved in the solvent. Then 1 atm of CO was introduced to it, then an agitation was carried out for 2~3 hours under 1 atm of CO, and then the volume of the solvent was reduced to 10 mL under a vacuum. Then the yellow precipitate was separated by adding 20 mL of diethylether. The yield of the final product was 90~94%.

EXAMPLE 11

Synthesis of Catalyst 11 ([IrCp*(CH$_3$CN)$_3$](OTf)$_2$)

A [IrCp*Cl$_2$]$_2$ compound in an amount of 0.5 g (0.628 mmol) (Cp*=pentamethyl cyclopentadienyl) and a solvent (acetonitrile) in an amount of 50 mL were put into a 100-mL one-sphere flask having an arm, so that the compound was dissolved in the solvent. Then 0.5 g (2.512 mmol) of AgOTf was added to it, then an agitation was carried out for 1 hour, and then the volume of the solvent was reduced to 10 mL under a vacuum. Then the yellow precipitate was separated by adding 20 mL of diethylether. The yield of the final product was 90~93%.

EXAMPLE 12

Synthesis of Catalyst 12 ((Cp*Cl$_2$Ir)(Ph)P[CH$_2$CH$_2$PPh$_2$IrCp*Cl$_2$]$_2$)

A [IrCp*Cl$_2$]$_2$ compound in an amount of 0.5 g (0.628 mmol) (Cp*=pentamethyl cyclopentadienyl) and a solvent (methylene chloride) in an amount of 50 mL were put into a 100-mL one-sphere flask having an arm, so that the compound was dissolved in the solvent. Then 0.224 g (0.419 mmol) of PhP[CH$_2$CH$_2$PPh$_2$]$_2$(TRIPHOS) was added to it, then an agitation was carried out for 5 hours, and then the volume of the solvent was reduced to 5 mL under a vacuum. Then the yellow precipitate was separated by adding 30 mL of diethylether. The yield of the final product was 80~85%.

Hydroformylation of Epoxide:

EXAMPLES 14~15 AND COMPARATIVE EXAMPLES 1~2

100 mL of water-saturated methyl-t-butyl ether (MTBE) was put into a 450 mL Parr reaction vessel at the ambient temperature. Then Co$_2$(CO)$_8$ in an amount of 2.5 mmol was added, and the catalyst 2 of Example 2 was put in mole ratios as shown in Table 1 below. The reaction vessel was put under a nitrogen atmosphere, and substitutions were carried out 3 times using CO/H$_2$(1/1). Then 11 g of ethylene oxide (EO) was put into the reaction vessel, and CO/H$_2$ (450/1050 psi) was supplied into the reaction vessel. Then the temperature was raised up to 80 degrees C., and then a reaction was carried out for time periods as shown in Table 1. During the reaction, the reaction mixture was sampled by means of a tube, and then the mixture of (3-hydroxypropanal) (HPA), 1,3-propanediol (1,3-PD), acetaldehyde (AA) and ethylene oxide (EO, starting material) was analyzed by using GC. After the reaction process, the temperature was cooled down to the ambient temperature, and then the catalyst was removed. Then the products, HPA and 1,3-PD, were separated and measured.

Comparative Examples 1–2 were carried out in the following manner. That is, they were carried out in the same manner as that of Example 14, except that triphenyl phosphine oxide (OPPh$_3$) was used as shown in Table 1, instead of catalyst 2. That is, ethylene oxide was hydroformylated, and then, the reaction mixture was analyzed. The analysis results are entered in Table 1, and the product HPA contained a small amount of 1,3-propanediol (1,3-PD). It can be seen that the catalytic activity and the selectivity (to HPA) of Examples 14–15 (in which a transition metal catalyst and a cobalt compound were used) are higher compared with Comparative Examples 1–2.

TABLE 1

| catalyst (promoter) | P/M[a] ratio | EO (g) | rxn time (hr) | conv. (%) | HPA selectivity (%) | HPA yield (%) | AA[b] (%) | TOF[c] |
|---|---|---|---|---|---|---|---|---|
| Example 14 | 2 | 1/15 | 11 | 1. | 89 | 91 | 81.0 | 9 | 45 |
| Example 15 | 2 | 1/15 | 11 | 1.5 | 96 | 86 | 82.6 | ~12 | 32 |
| Comp. Ex. 1 | OPPh$_3$ | 1/4 | 11 | 1.5 | 93 | 78 | 72.5 | 14 | 31 |
| Comp. Ex. 2 | OPPh$_3$ | 1/4 | 11 | 2 | 100 | 74 | 74.0 | 18 | 25 |

[a]P/M represents transition metal catalyst (promoter)/cobalt.
[b]AA represents acetaldehyde.
[c]TOF represents turn-over frequency (sub. mol/cat. mol/hr)

EXAMPLE 13

Synthesis of Catalyst 13 ((Cp*Cl$_2$Ir)P[CH$_2$CH$_2$PPh$_2$IrCp*Cl$_2$]$_3$)

A [IrCp*Cl$_2$]$_2$ compound in an amount of 0.5 g (0.628 mmol) (Cp*=pentamethyl cyclopentadienyl) and a solvent (methylene chloride) in an amount of 50 mL were put into a 100-mL one-sphere flask having an arm, so that the compound was dissolved in the solvent. Then 0.211 g (0.314 mmol) of P[CH$_2$CH$_2$PPh$_2$]$_2$(TETRAPHOS) was added to it, then an agitation was carried out for 5 hours, and then the volume of the solvent as reduced to 5 mL under a vacuum. Then the orange-colored precipitate was separated by adding 30 mL of diethylether. The yield of the final product was 80~85%.

EXAMPLES 16–20 AND COMPARATIVE EXAMPLES 3–6

A 10 mL of water-saturated methyl-t-butyl ether (MTBE) was put into a 45 mL Parr reaction vessel at the normal temperature. Then Co$_2$(CO)$_8$ in an amount of 0.25 mmol was added, and catalyst 2 of Example 2 was put in mole ratios as shown in Table 1. The reaction vessel was put under a nitrogen atmosphere, and substitutions were carried out for 3 times by using CO/H$_2$(1/1). Then ethylene oxide (EO) was put into the reaction vessel in amounts as shown in Table 2, and CO/H$_2$ (450/1050 psi) was supplied into the reaction vessel. Then the temperature was raised up to 80 degrees C., and then a reaction was carried out for time periods as shown in Table 2. After the reaction process, the temperature was cooled down to the ambient temperature, and then the catalyst was removed. Then the products, HPA and 1,3-PD, were separated and measured.

In Comparative Example 3, only the cobalt compound was used as the catalyst excluding catalyst 2. In Comparative Examples 4–6, instead of catalyst 2, triphenyl phosphine oxide ($OPPh_3$) was used in mole ratios as shown in Table 2. In Comparative Example 4, ethylene oxide was hydroformylated in the same manner as that of Example 16, except that MTBE containing less than 10 ppm of water was used, and that ethylene oxide was added in the amounts of Table 2. Then the synthesized products were analyzed. The analysis results are entered in Table 2 below, and the product HPA contained a small amount of 1,3-propanediol (1,3-PD). It can be confirmed that if the mole ratio (Ir/Co) is decided to be 1/15 among the transition metal catalysts as in the example 16 and 17, then the catalyst activity and the selectivity (to HPA) are superior over Comparative Examples 3–6.

TABLE 3

| Example | catalyst (promoter) | P/M[a] ratio | EO (g) | reaction time (hr) | HPA yield (%) |
|---|---|---|---|---|---|
| Example | | | | | |
| 16 | catalyst 2 | 1/15 | 1.1 | 1 | 65–66 |
| 17 | catalyst 2 | 1/15 | 1.18 | 1.5 | 81–83 |
| 18 | catalyst 2 | 1/30 | 1.22 | 3.5 | 59 |
| 19 | catalyst 2 | 1/10 | 0.95 | 1.5 | 63 |
| 20 | catalyst 2 | 1/6 | 0.89 | 1 | 59 |
| Comp. Ex. | | | | | |
| 3 | — | — | 0.91 | 2 | 23 |
| 4 | $OFPh_3$ | 1/4 | 1.01 | 2 | 47 |
| 5 | $OPPh_3$ | 1/4 | 1.06 | 1 | 30–40 |
| 6 | $OPPh_3$ | 1/4 | 1.05 | 2 | 70–73 |

[a] P/M represents transition metal catalyst (promoter)/cobalt.

EXAMPLES 21–38

A hydroformylation was carried out with varying the catalysts as shown in Table 3 below. These examples were carried out in the same manner as that of the example 14, except that the catalysts and the reaction time were varied. The analysis results are entered in Table 2, and the product HPA contained a small amount of 1,3-propanediol (1,3-PD). As can be confirmed in Table 3, when the catalysts of the present invention are used, the reactivity and the selectivity are superior to those of previous inventions.

TABLE 3

| Example | catalyst (promoter) | P/M[a] ratio | EO (g) | reaction time (hr) | HPA yield (%) |
|---|---|---|---|---|---|
| 21 | catalyst 1 | 1/15 | 1.95 | 1 | 72 |
| 22 | catalyst 1 | 1/15 | 1.06 | 2 | 76 |
| 23 | catalyst 3 | 1/15 | 1 | 1 | 45 |
| 24 | catalyst 3 | 1/15 | 1.01 | 2 | 63 |
| 25 | catalyst 4 | 1/15 | 0.94 | 2 | 52 |
| 26 | catalyst 5 | 1/15 | 1 | 2 | 52 |
| 27 | catalyst 6 | 1/15 | 1.02 | 2 | 82 |
| 28 | catalyst 7 | 1/15 | 0.9 | 2 | 78 |
| 29 | catalyst 8 | 1/15 | 0.9 | 2 | 66 |
| 30 | catalyst 9 | 1/15 | 0.9 | 2 | 66 |
| 31 | catalyst 10 | 1/15 | 1.03 | 2 | 78 |
| 32 | catalyst 11 | 1/15 | 1.06 | 1.5 | 73 |
| 33 | catalyst 12 | 1/15 | 1.01 | 2 | 53 |
| 34 | catalyst 13 | 1/15 | 0.97 | 2 | 58 |
| 35 | $[IrCp*Cl_2]_2$[b] | 1/15 | 1.18 | 1.5 | 53[d] |
| 36 | RhCp*-p[c] | 1/15 | 0.9 | 2 | 35 |
| 37 | RhCp*-p[c] | 1/8 | 0.97 | 2 | 41[d] |
| 38 | RhCp*-p[c] | 1/4 | 0.95 | 2 | 48[d] |

[a] P/M represents transition metal catalyst (promoter)/cobalt.
[b] $[IrCpCl_2]_2$ is a product of STREM company.
[c] RhCp*-p: $RhCp*Cl_2(PPh_2CH_2CH_2CH_2CH_2PPh_2)RhCp*Cl_2$.
[d] Oligomers were observed in GC chromatogram.

EXAMPLE 39

An $[IrCp*Cl_2]_2$ compound was put into a 10 mL of water saturated MTBE in 45 mL Parr reactor instead of putting catalyst 1 which was separated after the synthesis. Then a reflux was carried out for 24 hours together with $PPh_2CH_2CH_2CH_2CH_2PPh_2$ (diphenyl phosphinobutane), and then a 0.25 mmol of $Co_2(CO)_8$ was added into the 45 mL Parr reactor without separating the synthesized catalyst 1. Then a catalytic reaction was carried out. Except the above described process steps, Example 39 was carried out in the same manner as that of Example 22. The result was the same as that of Example 22.

An $[IrCp*Cl_2]_2$ compound was put into the MTBE instead of using catalyst 10 which was separated after the synthesis. Then a reflux was carried out for 5 hours under a CO atmosphere, and then a 0.25 mmol of $Co_2(CO)_8$ was added into the resulting solution of catalyst 10. Then a catalytic reaction was carried out. Except the above described process steps, Example 40 was carried out in the same manner as that of Example 31. The result was almost the same as that of Example 31.

EXAMPLES 41~43 AND COMPARATIVE EXAMPLES 7~9

In Examples 41~43, the hydroformylation was carried out in the same manner as that of Example 14, except that the kinds of the epoxide derivatives were conducted. In carrying out Comparative Examples 7–9, the catalyst, i.e., the triphenyl phosphine oxide ($OPPh_3$) was used at ratios as shown in Table 4 below. Except this, Comparative Examples 7–9 were carried out in the same manner as those of Examples 41–43. That is, ethylene oxide was hydroformylated, and the synthesized products were analyzed. The products contained tiny amounts of isomeric ketone compounds. The yields shown in Table 4 are the ones in which the solvent, the catalyst and auxiliary products have been removed. The results are shown in Table 4 below. It is seen that when the catalyst 2 is used together with the cobalt compounds, then the catalyst activity becomes superior.

TABLE 4

| | epoxide (mmol) | catalyst (promoter) | P/M ratio | reaction time (hr) | yield (%) |
|---|---|---|---|---|---|
| Example | | | | | |
| 41 | propylene oxide (2.5) | catalyst 2 | 1/15 | 2 | 92 |
| 42 | 1-butene oxide (2.5) | catalyst 2 | 1/15 | 2 | 91 |
| 43 | 1-hexene oxide (2.5) | catalyst 2 | 1/15 | 2 | 64 |

TABLE 4-continued

|  | epoxide (mmol) | catalyst (promoter) | P/M ratio | reaction time (hr) | yield (%) |
|---|---|---|---|---|---|
| Comp. Ex. | | | | | |
| 7 | propylene oxide (2.5) | OPPh$_3$ | 1/4 | 2 | 76 |
| 8 | 1-butene oxide (2.5) | OPPh$_3$ | 1/4 | 2 | 74 |
| 9 | 1-hexene oxide (2.5) | OPPh$_3$ | 1/4 | 5 | 50 |

EXAMPLE 44

100 mL of water-saturated methyl-t-butyl ether (MTBE) was put into a 450 mL Parr reaction vessel at the ambient temperature. Then 0.85 g of cobalt and 0.22g of catalyst 2 of Example 2 were added. The reaction vessel was put in a nitrogen atmosphere, and then, substitutions were carried out 3 times by using CO/H$_2$(1/1). The ethylene oxide was put in an amount of 11 g, and then, CO/H$_2$ (450/1050 psi) was supplied. The temperature was raised up to 80 degrees C., and the reaction was carried out for 1.5 hours. After the reaction, the temperature was cooled down to the ambient temperature, and then the product was extracted by using water under a nitrogen atmosphere. Then the yield was measured. After the extraction, the MTBE solution containing the catalyst was put into the reaction vessel again, and a catalytic reaction was carried out. Here, the yield was 82.6% like in the example 15. When the catalyst for the second time, the yield after 1.5 hours was 82%. When the catalyst was used for the third time, fourth time and fifth time, the yield was about 72%, 65% and 57%, respectively, after the reaction of 2 hours. This shows that the catalyst reactivity and the selectivity to HPA are high even after several uses.

EXAMPLE 45

A 100 mL of water-saturated methyl-t-butyl ether (MTBE) was put into a 450 mL Parr reaction vessel at the ambient temperature. Then 0.85 g of cobalt and 0.15 g of the catalyst 10 of the example 10 were added. The reaction vessel was put in a nitrogen atmosphere, and then, substitutions were carried out 3 times by using CO/H$_2$(1/1). The ethylene oxide was put in an amount of 11 g, and then, CO/H$_2$ (450/1050 psi) was supplied. The temperature was raised up to 80 degrees C., and the reaction was carried out for 1.5 hours. After the reaction, the temperature was cooled down to the ambient temperature, and then the product was extracted by using water under a nitrogen atmosphere. Then the yield was measured. After the extraction, the MTBE solution containing the catalyst was put into the reaction vessel again, and a catalytic reaction was carried out. Here, the yield was 81%. When the catalyst was used for the second time, the yield after a 2-hour reaction was 82%–84% which is higher that of Example 31. When the catalyst was used for the third time, fourth time and fifth time, the yields were respectively about 76%, 69% and 59% after the reaction of 2 hours. This shows that the catalytic activity and the selectivity to HPA are high even after the use of several times.

COMPARATIVE EXAMPLE 10

150 mL of water-saturated methyl-t-butyl ether (MTBE) was put into a 450 mL Parr reaction vessel at the ambient temperature. Then 0.87 g of cobalt and 0.40 g of OPPh$_3$ were added. The reaction vessel was put in a nitrogen atmosphere, and then, substitutions were carried out 3 times by using a CO/H$_2$(1/1) mixture gas. The ethylene oxide was put in an amount of 11 g, and then, CO/H$_2$ (450/1050 psi) was supplied. The temperature was raised up to 80 degrees C., and the reaction was carried out for 2 hours. After the reaction, the temperature was cooled down to the ambient temperature, and then the product was extracted by using water under a nitrogen atmosphere. Then the yield was measured. After the extraction, the MTBE solution containing the catalyst was put into the reaction vessel again, and a catalytic reaction was carried out. Here, the yield was 73% like in the comparative example 2. When the catalyst was used for the second time, third time, fourth time and fifth time, the yields were respectively about 71%, 64%, 58% and 51% after the reaction of 2 hours. Thus the catalytic activity and the selectivity to HPA were low compared with Examples 44 and 45.

Hydroesterification of Epoxide:

EXAMPLES 46–49

Temperature Effect on the Hydroesterification of Ethylene Epoxide (EO)

The catalyst Co$_2$(CO)$_8$ was put in an amount of 85 mg (0.25 mmol) into a nitrogen-substituted 45 mL Parr high pressure reaction vessel, and then, 10 mL of methanol (MeOH) was put to dissolve it. For the sake of a quantitative comparison, the amount of the cobalt catalyst was shown in the m mole unit of the metal atoms. Then 1.1 g (25 mmol) of ethylene oxide (EO) was put into the reaction vessel. Then CO gas was supplied into the reaction vessel until its internal pressure became 500 psi. Then an agitation was carried out while the temperature was raised up to the reaction level. The reaction was carried out for 2 hours, and then, the temperature was cooled down to the ambient temperature, while removing the residual gas. Then the product was recovered by removing the metal components from the reaction mixture. The product was analyzed by using a chromatography (GC), and the results are shown in Table 5 below. As shown in Table 5, when the temperature was varied within the range of 50–100 degrees C., as the temperature became higher, so much the yield was increased. However, if the temperature was too high, the yields of the by-products were also increased. Thus 80 degrees C. was the optimum reaction temperature.

TABLE 5

| | | | | Product Selectivity (%) | | |
|---|---|---|---|---|---|---|
| Example | reaction temp. (° C.) | EO conv. rate | MHP yield (g) | MHP[a] | MOE[b] | AA, OG, Other[c] |
| 46 | 50 | 10 | 0.25 | 96 | small | 3 |
| 47 | 60 | 12 | 0.30 | 95 | small | 4 |
| 48 | 80 | 28 | 0.68 | 94 | 2 | 4 |
| 49 | 100 | 36 | 0.80 | 85 | 7 | 8 |

[a] MHP represents methyl 3-hydroxypropionate.
[b] MOE represents 2-methoxyethanol (HO(CH$_2$)$_2$OMe).
[c] AA represents acetaldehyde, OG represents oligomers and Other represents unkown compounds

EXAMPLE 50–53

Temperature Effect on Hydroesterification of Propylene Epoxide (PO)

The catalyst $Co_2(CO)_8$ was put in an amount of 68 mg (0.20 mmol) into a nitrogen-substituted 45 mL Parr high pressure reaction vessel, and then, 10 mL of methanol (MeOH) was put to dissolve it. For the sake of a quantitative comparison, the amount of the cobalt catalyst was shown in the m mole unit of the metal atoms. Then 0.58 g (10 mmol) of propylene oxide (PO) was put into the reaction vessel. Then CO gas was supplied into the reaction vessel until its internal pressure became 1000 psi. Then an agitation was carried out while the temperature was raised up to the reaction level. In the case of Example 52, besides the cobalt catalyst, a promoter $K_2CO_3$ was added in an amount of 64 mg. The reaction was carried out for 15 hours, and then, the temperature was cooled down to the ambient temperature, while removing the residual gas. Then the product was recovered by removing the metal components from the reaction mixture. The product was analyzed by using a chromatography (GC), and the results are shown in Table 6 below. Like in the case of ethylene oxide, the desirable reaction temperature was 80 degrees C., and the results were similar whether the promoter was used (Example 52) or not (Example 51).

TABLE 6

| Example | reaction temp. (° C.) | PO conv. rate (%) | MHB[a] yield (g) | (Product Selectivity) (%) | | |
|---|---|---|---|---|---|---|
| | | | | acetone | MHB[a] | MOP[b] |
| 50 | 50 | 28 | 0.33 | — | ~99 | — |
| 51 | 80 | 96 | 1.08 | — | 95 | 4 |
| 52 | 80 | 91 | 1.01 | — | 94 | 5 |
| 53 | 100 | 100 | 0.77 | 18 | 65 | 17 |

[a] MHB represents methyl 3-hydroxybutyrate ($CH_3CH(OH)CH_2CO_2CH_3$).
[b] MOP represents 2-propanol ($CH_3CH(OH)CH_2(OMe)$).

EXAMPLES 54–59

Effect of Pressure on Hydroesterification

These examples were carried out in the same manner as that of Examples 46–49, except that the reaction temperature was fixed to 80 degree C., and that the pressure of carbon monoxide was varied as shown in Table 7 below. The results are shown in Table 7. The results of the examples 54–56 show that as the reaction time is increased, so much the amount of the product MHP (methyl 3-hydroxypropionate) increases. In Examples 57–59, the variations of the yields of the products versus the variation of the pressure of carbon monoxide are seen.

TABLE 7

| Example | rxn. time (hr) | Pco (psi) | EO conv. rate (%) | MHP yield (g) | Product Selectivity (%) | | |
|---|---|---|---|---|---|---|---|
| | | | | | MHP[a] | MOE[b] | AA, OG, Other[c] |
| 54 | 2 | 500 | 28 | 0.68 | 94 | 2 | 4 |
| 55 | 4 | 500 | 66 | 1.58 | 92 | 3 | 5 |
| 56 | 12 | 500 | 94 | 2.12 | 88 | 4 | 8 |
| 57 | 6 | 500 | 81 | 1.90 | 90 | 3 | 7 |
| 58 | 2 | 300 | 29 | 0.72 | 93 | 2 | 5 |
| 59 | 2 | 1500 | 13 | 0.31 | 91 | 2 | 7 |

[a] MHP represents methyl 3-hydroxypropionate.
[b] MOE represents 2-methoxyethanol ($HO(CH_2)_2OMe$).
[c] AA represent acetaldehyde, oligomers and Other represents unknown compounds

EXAMPLES 60–64

Effect of Solvent on Hydroesterification

The catalyst $Co_2(CO)_8$ was put in an amount of 68 mg (0.20 mmol) into a nitrogen-substituted 45 mL Parr high pressure reaction vessel, and then 10 mL of a solvent, methanol (MeOH) was put to dissolve it. For the sake of a quantitative comparison, the amount of the cobalt catalyst was shown in the m mole unit of the metal atoms. Then 0.58 g (10 mmol) of propylene oxide (PO) was put into the reaction vessel. Then CO gas was supplied into the reaction vessel until its internal pressure became 1000 psi. Then agitation was carried out while the temperature was raised up to 80 degrees C. The reaction was carried out for 15 hours, and then, the temperature was cooled down to the ambient temperature, while removing the residual gas. Then the product was recovered by removing the metal components from the reaction mixture. The product was analyzed by using a chromatography (GC), and the results are shown in Table 8 below.

TABLE 8

| Example | solvent[a] | PO conv. rate (%) | MHB yield (g) | (Product Selectivity) (%) | | | |
|---|---|---|---|---|---|---|---|
| | | | | acetone | MHB[b] | MMHP[c] | MOP[d] |
| 60 | MeOH | 96 | 1.08 | <1 | 95 | — | 4 |

TABLE 8-continued

| | solvent[a] | PO conv. rate (%) | MHB yield (g) | (Product Selectivity) (%) | | | |
|---|---|---|---|---|---|---|---|
| | | | | acetone | MHB[b] | MMHP[c] | MOP[d] |
| 61 | Et$_2$O | 19 | 0.22 | — | 99 | — | — |
| 62 | THF | 95 | 1.01 | <1 | 90 | 5 | 4 |
| 63 | MTBE | 20 | 0.23 | — | 99 | — | — |
| 64 | DME | 86 | 0.97 | <1 | 96 | — | 3 |
| Comp. Ex. | | | | | | | |
| 11 | MC | <5 | — | — | small | — | — |

[a] 2 mL of MeOH was mixed into each 8 mL of the solvent.
[b] MHB represents methyl 3-hydroxybutyrate (CH$_3$CH(OH)CH$_2$CO$_2$CH$_3$).
[c] MMHP represents methyl 2-methyl-3-hydroxypropionate (HOCH$_2$CH(CH$_3$)CO$_2$CH$_3$).
[d] MOP represents 1-methoxy-2-propanol (CH$_3$CH(OH)CH$_2$(OMe)).

Example 60 in which methanol was used showed an excellent PO conversion rate, and an excellent MHB (methyl 3-hydroxybutyrate) selectivity. In Example 61 in which diethylether was used, and in Example 63 in which methyl-t-butylether was used, the selectivity of the product was superior, but the reaction speed was slow. In most of the solvents, CO insertion reactions occurred selectively at the portions where PO was less substituted (the position a of formula 1), but under THF (Example 62), the reaction was proceeded even at the portion where there are many substitution radicals (the position b of formula 1). Thus MMHP (methyl 2-methyl-3-hydroxy propionate) was formed by about 5%. In the comparative example in which dichloromethanol was used, it was confirmed that almost no reaction occurred.

Reaction 1:

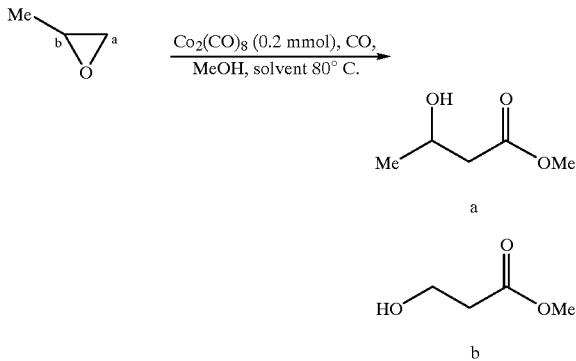

EXAMPLES 65~67

Hydroesterification of Various Epoxide Derivatives

The catalyst Co$_2$(CO)$_8$ was put in an amount of 68 mg (0.20 mmol) into a nitrogen-substituted 45 mL Parr high pressure reaction vessel, and then, 10 mL of a solvent, i.e., methanol (MeOH) was put to dissolved it. For the sake of a quantitative comparison, the amount of the catalyst was shown in the m mole unit of the metal atoms. Then epoxide was added as shown in Table 9. Then CO gas was supplied into the reaction vessel until its internal pressure became 1000 psi. Then an agitation was carried out while the temperature was raised up to 80 degrees C. The reaction was carried out for 15 hours, and the temperature was cooled down to the ambient temperature, and removed the residual gas. Then the product was recovered by removing the metal components from the reaction mixture. The product was analyzed by using a chromatography (GC), and the results are shown in Table 9 below.

TABLE 9

| Example | epoxide | conv. rate (%) | main product[a] yield (g) | (Product Selectivity) (%) | | |
|---|---|---|---|---|---|---|
| | | | | main[a] | by-product[b] | isomer[c] |
| 65 | 1-butene oxide (BO) | 97 | 1.18 | 92 | 8 | small |
| 66 | 1-hexene oxide (HO) | 79 | 1.15 | 91 | 6 | 3 |
| 67 | allylbenzene oxide | 95 | 1.77 | 96 | 4 | small |

[a] The main products,
[b] by products and
[c] isomers for the respective epoxides are shown in Table 10 below.
Most of the by-products were formed in such a manner that methanol directly attacks the substrate. Almost no CO reaction occurred at the portion of the substrate where there are substitution radicals.

TABLE 10

| a) main product | b) by-product | c) isomer |
|---|---|---|
| 1-BO CH$_3$CH$_2$CH(OH)CH$_2$CO$_2$Me | CH$_3$CH$_2$CH(OH)CH$_2$(OMe) | methylethylketone |
| 1-HO CH$_3$(CH$_2$)$_3$CH(OH)CH$_2$CO$_2$Me | CH$_3$(CH$_2$)$_3$CH(OH)CH$_2$(OMe) | 2-hexanone |
| ABO C$_6$H$_5$CH$_2$CH(OH)CH$_2$Me | C$_6$H$_5$CH$_2$CH(OH)(OMe) | methylbenzylketone |

According to the present invention as described above, in the hydroformylation, 3-hydroxyaldehyde derivatives can be synthesized from the epoxide derivatives with high catalytic activity and selectivity, compared with the conventional technique in which only the cobalt catalyst in addition to a known promoter are used. Unlike the conventional catalyst containing the phosphinic compound, the catalyst of the present invention makes it easy to recover and regenerate. Meanwhile, in the hydroesterification of the present invention, 3-hydroxyester derivatives can be synthesized with a high selectivity and a high yield by reacting CO with an alcohol at the presence of a proper solvent and a cobalt catalyst at a reaction temperature of 30–130 degrees C. at a CO pressure of 100–3000 psi.

It should be apparent to those ordinarily skilled in the art that various changes and modifications can be added without departing from the scope of the present invention.

What is claimed is:

1. A neutral or cationic transition metal catalyst for use in a hydroformylation of epoxide derivatives comprising a compound represented as formula (A-2) or a compound synthesized from the reaction of (A-2) with a compound having one or more active radicals:

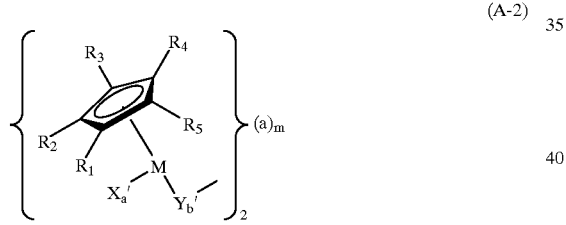

(A-2)

wherein:

M represents Ir having an oxidation state of 1 or 3;

(a) is a 1-valence anion of BF$_4$—, PF$_6$—, ClO$_4$—, SO$_3$CF$_3$— or BR'$_4$— or a 2-valence anion of CO$_3^{2-}$ or SO$_4^{2-}$ R' represents hydrogen; an alkyl radical of saturated or unsaturated aliphatic chain type or ring type hydrocarbons or aromatic hydrocarbons having C$_1$~C$_{10}$; or a halogen atom of F, Cl, Br or I;

m is an integer of 0, 2 or 4 when (a) is a 1-valence anion or a halogen atom, and m is 0, 1 or 2 when (a) is a 2-valence anion;

R$_1$~R$_5$ are each independently selected from hydrogen; saturated or unsaturated aliphatic or aromatic hydrocarbons of C$_1$~C$_{20}$; saturated or unsaturated aliphatic or aromatic hydrocarbons having nitrile radicals at the end or at the middle; saturated or unsaturated aliphatic or aromatic hydrocarbons having amine radicals at the end or at the middle; and halogen atoms of F, Cl, Br or I;

a' and b' in X$_{a'}$ and Y$_{b'}$ are integers of 0~2, with a'+b'=2;

X$_{a'}$ is a halogen atom of F, Cl, Br or I; a hydroxy radical; an alkoxy including a saturated or unsaturated aliphatic or aromatic hydrocarbon of C$_1$~C$_{10}$; a nitrile including saturated or unsaturated aliphatic or aromatic hydrocarbons of C$_1$~C$_{10}$; or a compound expressed by the formulas (I), (II) or (III):

(I)

(II)

(III)

Q$_1$ is N, P, As or Sb;

Q$_2$ and Q$_3$ are each independently selected from P, As or Sb;

Rc, Rd and Re are each independently selected from hydrogen; alkyl radicals including saturated or unsaturated aliphatic or aromatic chain type or ring type hydrocarbons of C$_1$~C$_{20}$, or aromatic hydrocarbons; aliphatic hydrocarbons having carbon chains of of C$_1$~C$_5$; cyclohexyl; phenyl; benzyl; compounds including at least one or more nitrile radicals, amine radicals having a formula R$_f$R$_g$N—, aldehyde radicals or ketone radicals in an aliphatic hydrocarbon or in a phenyl or in a benzyl; halogen atoms of F, Cl, Br or I; phosphine radicals; arsine radicals; or stibine radicals including saturated or unsaturated aliphatic or aromatic chain type or ring type hydrocarbons or aromatic hydrocarbons of C$_1$~C$_{30}$;

c, d, and e in the Rc, Rd and Re, are integers of 0~3, with c+d+e=3;

R$_f$ and R$_g$ are each independently selected from hydrogen; and alkyl radicals including saturated or unsaturated aliphatic or aromatic chain type or ring type hydrocarbons of C$_1$~C$_{20}$, aliphatic hydrocarbons, carbon chains of C$_1$~C$_{10}$ having no branches, carbon chains having branches, or ring type compounds;

f and g are integers of 0~2, with f+g=2; and

Y$_{b'}$ is carbon monoxide; a halogen atom of F, Cl, Br or I; a hydroxy radical; or an alkoxy radical including saturated or unsaturated aliphatic or aromatic hydrocarbons of C$_1$~C$_{10}$.

2. The transition metal catalyst as claimed in claim 1, wherein said compound having one or more active radicals is represented as formulas (B-1), (B-2) or (B-3):

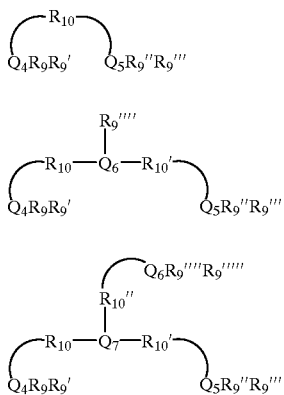

(B-1)

(B-2)

(B-3)

wherein:

$Q_4$, $Q_5$, $Q_6$ and $Q_7$ are each independently selected from N, P, As or Sb;

$R_9$, $R_9'$, $R_9''$, $R_9'''R_9''$, $R_9''''$ are each independently selected from hydrogen; aliphatic hydrocarbons, aromatic hydrocarbons, or both of the aliphatic and aromatic hydrocarbons of $C_1 \sim C_{20}$; aliphatic hydrocarbons including $C_1 \sim C_5$ carbon chains or cyclohexyl; phenyl; benzyl; compounds including at least one nitrile radical, amine radical having a formula of $R_f R_g N-$, aldehyde radical or ketone radical in an aliphatic hydrocarbon or in a phenyl or in a benzyl; halogen atoms of F, Cl, Br or I; and phosphine radicals, arsine radicals or stibine radicals including aliphatic or aromatic chain type or ring type hydrocarbons or aromatic hydrocarbons of $C_1 \sim C_{30}$;

$R_F$ and $R_g$ are each independently selected from hydrogen; or alkyl radicals including saturated or unsaturated aliphatic or aromatic chain type or ring type hydrocarbons of $C_1 \sim C_{20}$, aliphatic hydrocarbons, carbon chains of $C_1 \sim C_{10}$ having no branches, carbon chains having branches, ring type compounds, or aliphatic hydrocarbons;

f and g are integers of 0~2, with f+g=2; and $R_{10}$, $R_{10}'$ and $R_{10}''$ are each independently selected from alkyl radicals including carbon chains of saturated or unsaturated aliphatic chain type or ring type hydrocarbons or aromatic hydrocarbons having $C_1 \sim C_{20}$, carbon chains of $C_1 \sim C_{10}$ having no branches, carbon chains having branches, ring type compounds, or aromatic hydrocarbons.

3. The transition metal catalyst as claimed in claim 1, wherein the transition metal catalyst is represented by formulas (C-1), (C-2), (C-3), (C-4) or (C-5):

(C-1)

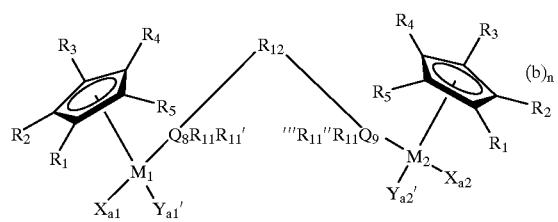

(C-2)

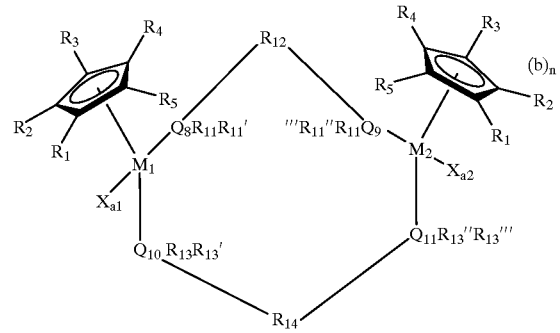

(C-3)

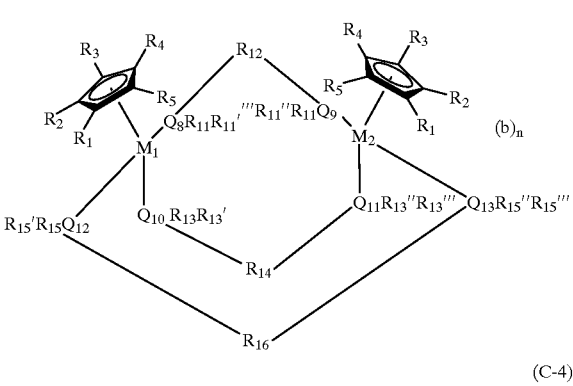

(C-4)

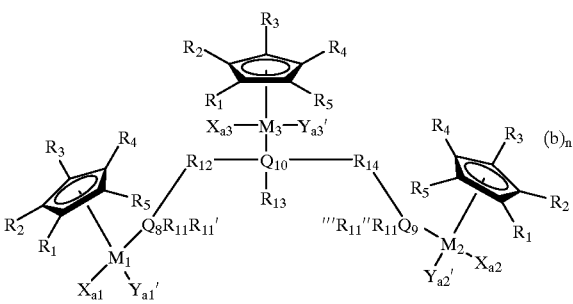

(C-5)

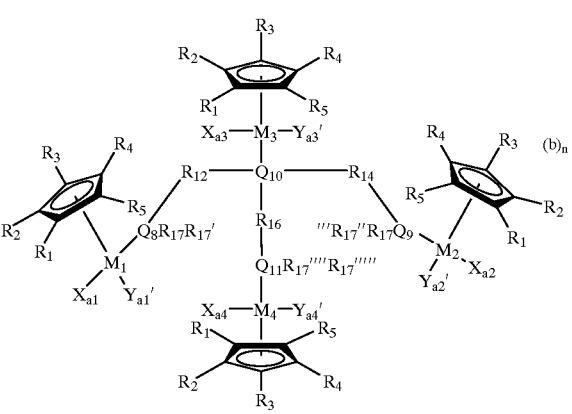

$M_1$, $M_2$, $M_3$ and $M_4$ are each independently Ir having an oxidation state of 1 or 3;

(b) is a 1-valence anion of $BF_4-$, $PF_6-$, $ClO_4-$, $SO_3CF_3-$ or $BR'_4-$ or a 2-valence anion of $CO_3^{2-}$ or $SO_4^{2-}$ R' represents hydrogen; an alkyl radical of saturated or unsaturated aliphatic chain type or ring type hydrocarbons or aromatic hydrocarbons having $C_1$~$C_{10}$; or a halogen atom of F, Cl, Br or I;

a2, a2, a3, and a4 are integers of 0~2, and a1', a2', a3' and a4' are integers of 0~2, with a1+a1'=2, a2+a2'=2, a3+a3'=2, and a4+a4'=2;

$X_{a1}$, $X_{a2}$, $X_{a3}$ and $X_{a4}$, and $Y_{a1'}$, $Y_{a2'}$, $Y_{a3'}$ and $Y_{a4'}$ are each independently selected from carbon monoxide; halogen atoms of F, Cl, Br or I; hydroxy radicals; aliphatic or aromatic hydrocarbons having no branch at $C_1$~$C_{10}$; aliphatic or aromatic hydrocarbons having at least one branch at $C_1$~$C_{10}$; hydroxy radicals including aliphatic or aromatic hydrocarbons with at least one branch at $C_1$~$C_{10}$; saturated or unsaturated aromatic hydrocarbons of $C_1$~$C_{10}$, or nitrile including aliphatic hydrocarbons with saturated or unsaturated aliphatic chains; ketones including aliphatic hydrocarbons or aliphatic chain type or ring type hydrocarbons of $C_1$~$C_{20}$; ethers including aliphatic hydrocarbons or aliphatic chain type or ring type hydrocarbons of $C_1$~$C_{20}$; amines expressed by $N(R_6)(R_7)(R_8)$; pyrrole, pyrazine, pyrazole, imidazole, pyrimidine, piperidine, pyridine or their derivatives, all of them having $C_3$~$C_{30}$; or compounds expressed by the following formulas, or their mixtures:

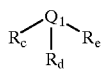

(I)

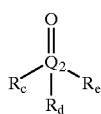

(II)

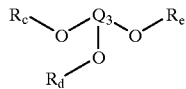

(III)

$Q_8$, $Q_9$, $Q_{10}$, $Q_{11}$, $Q_{12}$ and $Q_{13}$ are each independently selected from N, P As or Sb;

$R_{11}$, $R_{11}'$, $R_{11}''$, $R_{11}'''$, $R_{13}$, $R_{13}'$, $R_{13}''$, $R_{13}'''$, $R_{15}$, $R_{15}'$, $R_{15}''$, $R_{15}'''$, $R_{17}$, $R_{17}'$, $R_{17}''$, $R_{17}'''$, $R_{17}''''$ and $R_{17}'''''$ respectively are each independently selected from hydrogen; aliphatic hydrocarbons, aromatic hydrocarbons, or both of the aliphatic and aromatic hydrocarbons of $C_1$~$C_{20}$; aliphatic hydrocarbons including $C_1$~$C_5$ carbon chains or cyclohexyl; phenyl; benzyl; compounds including at least one nitrile radical, amine radical having a formula of $R_fR_gN$—, aldehyde radical or ketone radical in an aliphatic hydrocarbon or in a phenyl or in a benzyl; halogen atoms of F, Cl, Br or I; and phosphine radicals, arsine radicals or stibine radicals including aliphatic or aromatic chain type or ring type hydrocarbons or aromatic hydrocarbons of $C_1$~$C_{30}$;

$R_{12}$, $R_{14}$ and $R_{16}$ are each independently selected from alkyl radicals including carbon chains of saturated or unsaturated aliphatic chain type or ring type hydrocarbons or aromatic hydrocarbons having $C_1$~$C_{20}$, carbon chains of $C_1$~$C_{10}$ having no branches, carbon chains having branches, ring type compounds, or aromatic hydrocarbons; and n is an integer of 0–8 when (b) is a 1-valence anion, and n is an integer of 0–4 when (b) is a 2-valence anion.

* * * * *

UNITED STATES PATENT AND TRADEMARK OFFICE
CERTIFICATE OF CORRECTION

PATENT NO. : 6,348,611 B1
DATED : February 19, 2002
INVENTOR(S) : Byeong-No Lee, Duck-Joo Yang and Young-Hun Byun It is certified that error appears in the above-identified patent and that said Letters Patent is hereby corrected as shown below:

Column 1,
Line 27, "derivatives" should read -- derivative --

Column 4,
Line 17, "ether" should read -- either --

Column 15,
Line 20, "TABLE 3" should read -- TABLE 2 --
Line 65, delete "$^{d)}$" after "53"
Line 66, after "35" insert -- $^{d)}$ --

Column 16,
Line 26, insert "EXAMPLE 40"

Column 27,
Line 5, "a2" should read -- a1 --

Signed and Sealed this

Eleventh Day of June, 2002

Attest:

JAMES E. ROGAN
Attesting Officer
Director of the United States Patent and Trademark Office